United States Patent
Falk et al.

(10) Patent No.: US 7,277,051 B2
(45) Date of Patent: Oct. 2, 2007

(54) METHOD AND A UNIT FOR BEAM CONTROL OF AN ARRAY ANTENNA

(75) Inventors: Kent Falk, Gothenburg (SE); Ingmar Karlsson, Kallered (SE); Hans Lind, Savedalen (SE); Thomas Ridderstrale, Monlycke (SE); Morgan Andersson, Romelanda (SE)

(73) Assignee: Telefonaktiebolaget LM Ericsson (publ.), Stockholm (SE)

( * ) Notice: Subject to any disclaimer, the term of this patent is extended or adjusted under 35 U.S.C. 154(b) by 276 days.

(21) Appl. No.: 10/527,990

(22) PCT Filed: Sep. 30, 2002

(86) PCT No.: PCT/SE02/01781

§ 371 (c)(1),
(2), (4) Date: Mar. 21, 2005

(87) PCT Pub. No.: WO2004/030145

PCT Pub. Date: Apr. 8, 2004

(65) Prior Publication Data
US 2006/0164301 A1    Jul. 27, 2006

(51) Int. Cl.
*H01Q 3/00* (2006.01)

(52) U.S. Cl. .................................... 342/373; 342/377
(58) Field of Classification Search ............. 342/368, 342/372, 373, 377, 378, 383
See application file for complete search history.

(56) References Cited

U.S. PATENT DOCUMENTS

| | | | |
|---|---|---|---|
| 5,274,386 A | 12/1993 | Pellon | |
| 5,591,911 A | 1/1997 | Masuzawa et al. | |
| 5,831,168 A | 11/1998 | Shinomura et al. | |

OTHER PUBLICATIONS

International Search Report mailed May 8, 2003.

*Primary Examiner*—Dao L. Phan
(74) *Attorney, Agent, or Firm*—Nixon & Vanderhye P.C.

(57) ABSTRACT

A method of producing a digital beamformer signal by a number of antenna modules that are alike and by providing a system that implements the method. This is accomplished by introducing signal processing on each antenna module and by creating an asynchronous serial adding chain through the antenna modules to at least in part calculate the digital beamformer signal. Advantageous embodiments according to the invention perform time and space signal processing multiplexing to calculate additional digital beamformer signals.

18 Claims, 11 Drawing Sheets

METHOD AND A UNIT FOR BEAM CONTROL OF AN ARRAY ANTENNA

REFERENCE TO RELATED APPLICATION

This application is the US national phase of international application PCT/SE2002/001781 filed 30 Sep. 2002, the entire content of which is incorporated by reference.

TECHNICAL FIELD

The invention concerns communication or sensor array antennas and is more particularly directed to a method and apparatus of dynamically controlling one or more antenna beams of array antennas.

BACKGROUND

To attain a desired flexibility regarding coverage and/or frequency bandwidth in advanced communication systems or sensor systems such as a radar, large array antennas with controllable beamforming are required. Array antennas with a large number of antenna elements, irrespective of whether an analogue or digital beamforming is involved, will require an unwieldy amount of information transfer as each antenna element has to deliver its values to a beamformer. To enable flexibility and a reasonable cost efficiency, practically all beamforming today is done by means of digital signal processing.

Array antenna systems with digital beamforming used today are typically of high complexity resulting in high costs and high power consumption. A first example is a system where each antenna element feeds its radio frequency (RF) signal to a centralized beamformer that performs analogue to digital (A/D) conversion and the subsequent digital signal processing. A system according to this first example will quickly result in an unwieldy large RF coupling network as the number of antenna elements rise. Such a system would also require a very advanced signal processor.

In a second example each antenna element performs any necessary analogue preprocessing and the A/D conversion. Digital signal values from each antenna element will then have to be either directly connected with a central digital beamformer resulting in a very large number of cables and connectors, or be connected to the central digital beamformer by means of a digital data bus, which would require a very wide high-capacity data-bus, which would be very expensive. A system according to the second example would also require a very advanced central signal processor to calculate the desired beam or beams.

A third example is a hybrid system with both digital and analogue beamforming. The array antenna is divided into subunits, where each subunit comprises a more manageable number of antenna elements. The antenna elements of each subunit are beamformed together in an analogue manner before being A/D converted and transferred to a central digital beamforming unit. The third example is often considered a good compromise, but it does not give all of the advantages of digital beamforming. There would thus seem to be room for further improvement in the area of digital beamforming in array antennas with a large number of antenna elements.

SUMMARY

An object of the invention is to define a method and an array antenna unit which overcomes the above mentioned drawbacks.

Another object of the invention is to define a method of and an array antenna device, which is possible to manufacture in a cost efficient manner.

The aforementioned objects are achieved according to the invention by a method of producing a digital beamformer signal by a number of antenna modules that are alike and by providing a system that implements the method. This is accomplished by introducing signal processing on each antenna module and by creating an asynchronous serial adding chain through the antenna modules to at least in part calculate the digital beamformer signal. Advantageous embodiments according to the invention perform time and spatial signal processing multiplexing to calculate additional digital beamformer signals.

The aforementioned objects are also achieved by a method of producing a digital beamformer signal using output signals generated by an array of antenna elements in response to the reception of electromagnetic waves. Each antenna element is directly associated with an antenna module, each of which processes an output signal generated by a corresponding antenna element. According to the invention the method comprises a plurality of steps. In a first step each antenna module provides a working frequency signal from the output signal generated by the corresponding associated antenna element. In a second step each antenna module converts the working frequency signal to a complex digital antenna signal at a first data rate. In a third step each antenna module multiplies the complex digital antenna signal with a complex beam coefficient generating a complex beam element signal at a second data rate. The complex beam coefficients are most commonly not the same on all of the antenna modules, but are dependent on the desired beam and which antenna element in the array is associated with the antenna module. In a fourth step the generated complex beam element signals are asynchronously added in groups comprising at least two antenna modules. Thus a complex beam signal is formed by means of complex adders on the respective antenna modules being intercoupled to form respective serial asynchronous complex adding chains. And finally in a fifth step the digital beamformer signal is provided from the formed/generated complex beam signal.

In some versions the first data rate and the second data rate are the same. In other versions the second data rate is a multiple of the first data rate, and then the method suitably further comprises the step of changing the complex beam coefficient in pace with the second data rate in each antenna module to thereby at the first data rate generate a multiple of complex beam signals, each of which represents a predetermined beam.

In some versions the multiple of complex beam signals are time multiplexed on the serial asynchronous complex adding chains. In other versions each antenna module comprises further complex adders forming multiple serial asynchronous complex adding chains associated with each antenna module. Then the multiple of complex beam signals are spatially multiplexed on the multiple of serial asynchronous complex adding chains. In still other versions each antenna module comprises further adders forming multiple serial asynchronous complex adding chains associated with each antenna module, but then the multiple of complex beam signals are both spatially and time multiplexed on the multiple of serial asynchronous complex adding chains.

In the step of asynchronously adding the generated complex beam element signals, adding is performed on a group comprising all antenna modules in some versions while in other versions the antenna modules are divided into at least two groups, and then the step of providing the digital beamformer signal from the complex beam signal, additionally determines the complex beam signal from the digital beamformer signal of each group serial asynchronous complex adding chain.

One or more of the features of the above-described different methods according to the invention can be combined in any desired manner, as long as the features are not contradictory.

The aforementioned objects are also achieved according to the invention by an array antenna comprising at least two antenna elements arranged for reception of electromagnetic waves. The array antenna comprises a beamformer arranged to form at least one reception beam. According to the invention at least a part of the beamformer is directly associated with a respective antenna element. Each part of the beamformer that is directly associated with an antenna element, forms an antenna element module of that antenna element. An antenna element module comprises a receiver, an analog to digital converter and I/Q splitter, a multiplier, an element latch, and an asynchronous complex adder. The receiver is arranged to provide a working frequency signal. The analog to digital converter and I/Q splitter are arranged to transform the working frequency signal from the receiver into I and Q digital complex signals at a first data rate. The multiplier is arranged to multiply the complex digital I and Q signals with a complex beam coefficient to thereby form a complex beam element signal at a second data rate. The element latch is arranged to freeze the complex beam element signal by a clock signal to form a latched complex beam element signal. The asynchronous complex adder is arranged to add the latched complex beam element signal with an input complex part beam signal, forming an output complex part beam signal. Further the output part beam signals of one antenna element module is coupled to the input complex part beam signal of a further antenna element module thus forming a serial asynchronous summing path of the latched complex beam element signals of the antenna element modules generating a complex beam signal. The first antenna module in a serial asynchronous summing path will add a feed value as its input complex part beam signal, a feed value can be a test value or an initial value, for example the constant in the equation. The last antenna module in a serial asynchronous summing path will, as its output part beam signal, deliver either a complex beam signal representing a predetermined beam or a complex beam signal that needs additional processing to represent a predetermined beam. The latter case is when the serial asynchronous summing path in question only includes a subset of all of the antenna elements of the array antenna.

Advantageously the antenna further comprises a beam latch that is arranged to store the complex beam signal by the clock signal. The element latch and the beam latch are both clocked at the same time. In some embodiments the element latch and the beam latch are clocked at the first data rate. In other embodiments the element latch and the beam latch are clocked at the second data rate. The second data rate is then a multiple of the first data rate, and then the complex beam coefficient is changed in pace with the second data rate to thereby at the first data rate generate a multiple of complex beam signals, each of which represents a predetermined beam. Then also advantageously the multiple of complex beam signals can be time multiplexed on the serial asynchronous summing path. In still other embodiments the second data rate is a multiple of the first data rate. The complex beam coefficient is then changed in pace with the second data rate to thereby at the first data rate generate a multiple of complex beam element signals. Each of the complex beam element signals represents a predetermined beam. In such embodiments it is suitable that each of the antenna element modules further comprises one or more additional element latches, and one or more additional asynchronous complex adders. The one or more additional element latches are arranged to freeze a complex beam element signal by a clock signal to form one or more additional latched complex beam element signals at a third data rate. The one or more additional asynchronous complex adders are each arranged to add one of the one or more additional latched complex beam element signal with an input complex part beam signal, each forming an additional output complex part beam signal. Then each additional output part beam signal of one antenna element module is coupled to a corresponding additional input complex part beam signal of a further antenna element module thus forming one or more additional serial asynchronous summing paths of the one or more additional latched complex beam element signals of the antenna element modules generating one or more additional complex beam signals. The antenna further suitably then comprises one additional beam latch for each additional serial asynchronous summing path. Each additional beam latch is arranged to store the additional complex beam signal by the clock signal. The one or more additional element latches and the one or more beam latches are clocked at the same time. In some sub-embodiments the third data rate is the same as the first data rate. Each corresponding element latch and beam latch are thus clocked at the first data rate and all the complex beam signals are spatially multiplexed on the serial asynchronous summing path and on the one or more additional serial asynchronous summing paths. In other sub-embodiments the third data rate is a multiple of the second data rate and the element latch and the beam latch are clocked at the third data rate. Then all the multiple of complex beam signals are thus both spatially and time multiplexed on all of the serial asynchronous summing paths.

Advantageously all of the antenna element modules of the array antenna are comprised in all of the serial asynchronous summing paths, or the antenna element modules of the array antenna are divided into at least two groups. Each group having separate serial asynchronous summing paths. The complex beam signals are then fed into a central beamformer part for final computation of the corresponding beams.

The features of the above-described different embodiments of an array antenna system according to the invention can be combined in any desired manner, as long as no conflict occurs.

By providing a method for attaining a digital beamformer signal and an array antenna system according to the invention a plurality of advantages over prior art methods and systems are obtained. A primary purpose of the invention is to enable the construction of very large array antennas, in the range of hundreds to tens of thousands of antenna elements. According to the invention this is enabled primarily by moving a substantial part of the signal processing onto antenna modules that are in direct association/connection with respective antenna element. Further by keeping the antenna modules simple and alike by removing the need for different multiple clock signals, which is attained by the serial asynchronous complex adding chains, the antenna modules are interchangeable and cost efficiently manufacturable in large quantities. Other advantages of this invention will become apparent from the description.

BRIEF DESCRIPTION OF THE DRAWINGS

The invention will now be described in more detail for explanatory, and in no sense limiting, purposes, with reference to the following figures, in which.

DETAILED DESCRIPTION

In order to clarify the method and device according to the invention, some examples of its use will now be described in connection with FIGS. 1 to 8.

Figure 1:
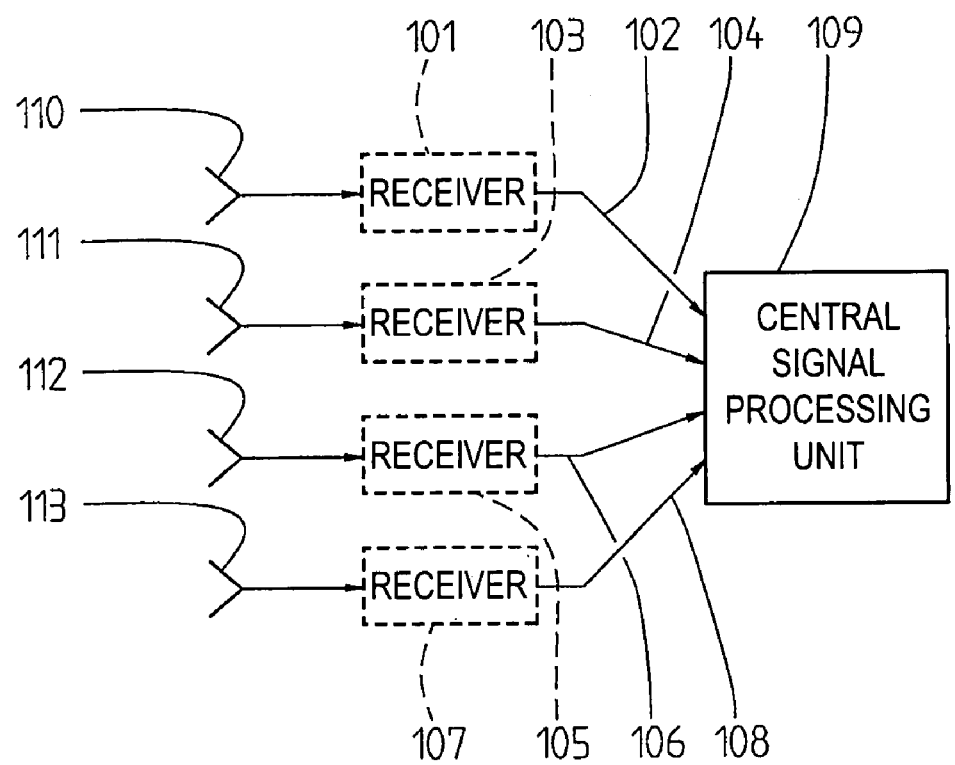
FIG. 1 illustrates an example of an array antenna system with a central signal processing unit.

FIG. 1 illustrates an example of an array antenna system with a central signal processing unit 109. The array antenna system comprises antenna elements 110, 111, 112, 113 that are either directly connected 102, 104, 106, 108, to the central signal processing unit 109, or connected 102, 104, 106, 108 via respective receivers 101, 103, 105, 107 that are arranged at or close to the antenna elements 110, 111, 112, 113. Such an array antenna system can be acceptable with a very limited number of antenna elements, say a maximum being in the range of tens of antenna elements. If the number of antenna elements rises, then the number of necessary connections 102, 104, 106, 108 becomes unmanageable, and the necessary computing power of the central signal processing unit 109 becomes very large. The acceptable upper limit of antenna elements will be higher if there are receivers and A/D converters associated with each antenna element, to thereby transport received values digitally. These reasons, and probably more so the offered flexibility, have turned focus away from analogue signal processing and towards digital signal processing instead. The ever emerging availability of faster, cheaper, and more accurate A/D converters and digital signal processors will play an important part in implementing large array antenna systems outside research laboratories.

An important aspect, according to the invention, to be able to implement large array antenna systems comprising antenna elements in the range of hundreds to tens of thousands, is to distribute the digital signal processing, i.e. to at least partly digitally process the received signals at or very close to each antenna element. The digital computations in themselves that are needed are relatively simple and according to the invention possible to distribute. To calculate a beam L, different complex coefficients $a_n$ that are associated with specific antenna elements n, the complex (I/Q) received signal $V_n$ of the N antenna elements, complex multipliers, and complex adders are needed. Expressed mathematically $L=\Sigma a_n \cdot V_n$ for n=1 to N. A distributed digital signal processing is also motivated by reduced bandwidth need, i.e. transfer capacity, between antenna elements and a central processing unit when the number of antenna elements becomes larger than the number of desired beams to be determined. This will most likely occur for array antennas with a hundred or more antenna elements. Therefore, according to the invention, the beamformer of an array antenna according to the invention is distributed, at least in part, to each one of the antenna elements to locally, at least partly, calculate the desired beams.

Figure 2A:
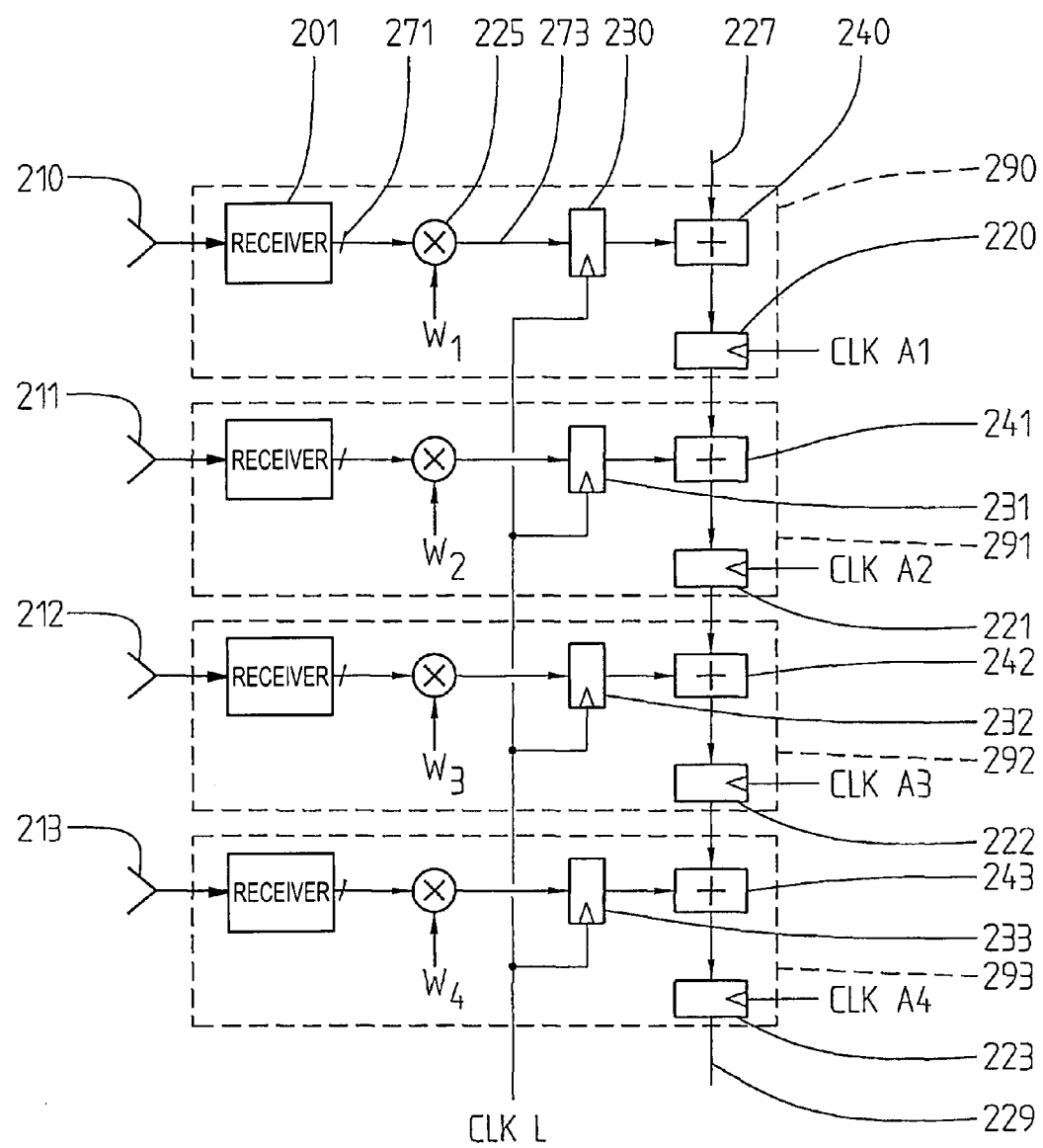
FIG. 2A illustrates an example of an array antenna with at least partial signal processing directly associated with each separate antenna element.

FIG. 2A illustrates an example of such an array antenna with at least partial signal processing directly associated with each separate antenna element 210, 211, 212, 213. References will also be made to FIG. 2B, which illustrates a timing diagram for the array antenna system according to FIG. 2A. Each antenna element 210, 211, 212, 213 has an antenna module 290, 291, 292, 293 associated with it, i.e. the antenna module 290, 291, 292, 293 is at or very close to its respective antenna element 210, 211, 212, 213. Each antenna module 290, 291, 292, 293 will typically comprise a receiver 201 that comprises an A/D converter and an I/Q splitter, to deliver a complex antenna signal 271, an I/Q antenna signal. The I/Q antenna signal 271 will then enter the beamformer digital signal processing, which first comprises a complex multiplier 225 that multiplies the I/Q antenna signal 271 with a beam specific and antenna module 290, 291, 292, 293 specific complex weight/coefficient $W_1$, $W_2$, $W_3$, $W_4$, to generate a complex beam element signal 273. The complex beam element signals 273 of each antenna module 290, 291, 292, 293 are latched into a corresponding multiplier latch 230, 231, 232, 233 on a positive clock edge 250, 259 of a latch clock CLK L when the multipliers 225 are assumed to be ready and have output values 273 that have settled. It is assumed in this application that latches will enter a value on positive clock edges.

In a first cycle, the multiplier latches 230, 231, 232, 233 are all loaded at a positive edge 250 of their clock signal CLK L. An adder 240 of the first antenna module 290 will then add the latched complex beam element signal in the multiplier latch 230 with a default value 227 since it is first in the adder chain. When it is assumed that the adder 240 has settled output values, i.e. has finished adding, then a positive edge 252 of the adder latch clock signal CLK A1 latches the result of the first antenna module 290 into its adder latch 220. An adder 241 of the second antenna module 291 will then add the value of its multiplier latch 231 with the result of the first antenna module 290. When it is assumed that the adder 241 has settled output values, then a positive edge 254 of the adder latch clock signal CLK A2 latches the result of the second antenna module 291 into its adder latch 221.

An adder 242 of the third antenna module 292 will then add the value of the multiplier latch 232 with a latched complex beam element signal with the result of the second antenna module 291. When the adder 242 has settled output values, then a positive edge 256 of the adder latch clock signal CLK A3 latches the result of the third antenna module 292 into its adder latch 222. Finally, as this example only comprises four antenna modules 290, 291, 292, 293, an adder 243 of the fourth antenna module 293 will then add the calculated value given by the third antenna module 292 with its latched complex beam element signal in its multiplier latch 233. After a predetermined time period, when it is assumed that the adder 243 has settled output values, then a positive edge 258 of the adder latch clock signal CLK A3 latches the result of the fourth antenna module 293 into its adder latch 223 giving the desired beamformed complex beam signal 229.

As is obvious from the above, all of the antenna modules 290, 291, 292, 293 require different clock signals CLK A1, CLK A2, CLK A3, CLK A4. The clock signals CLK A1, CLK A2, CLK A3, CLK A4 are further a multiple, the number of antenna modules 290, 291, 292, 293, higher in frequency than the rate of delivered complex beam signals 229. By interleaving the additions, the throughput can increase at the cost of even more and different clock signals for each specific antenna module 290, 291, 292, 293. Constructing an array antenna system with fifty or more antenna modules in an adding chain would be very difficult.

Figure 3A:
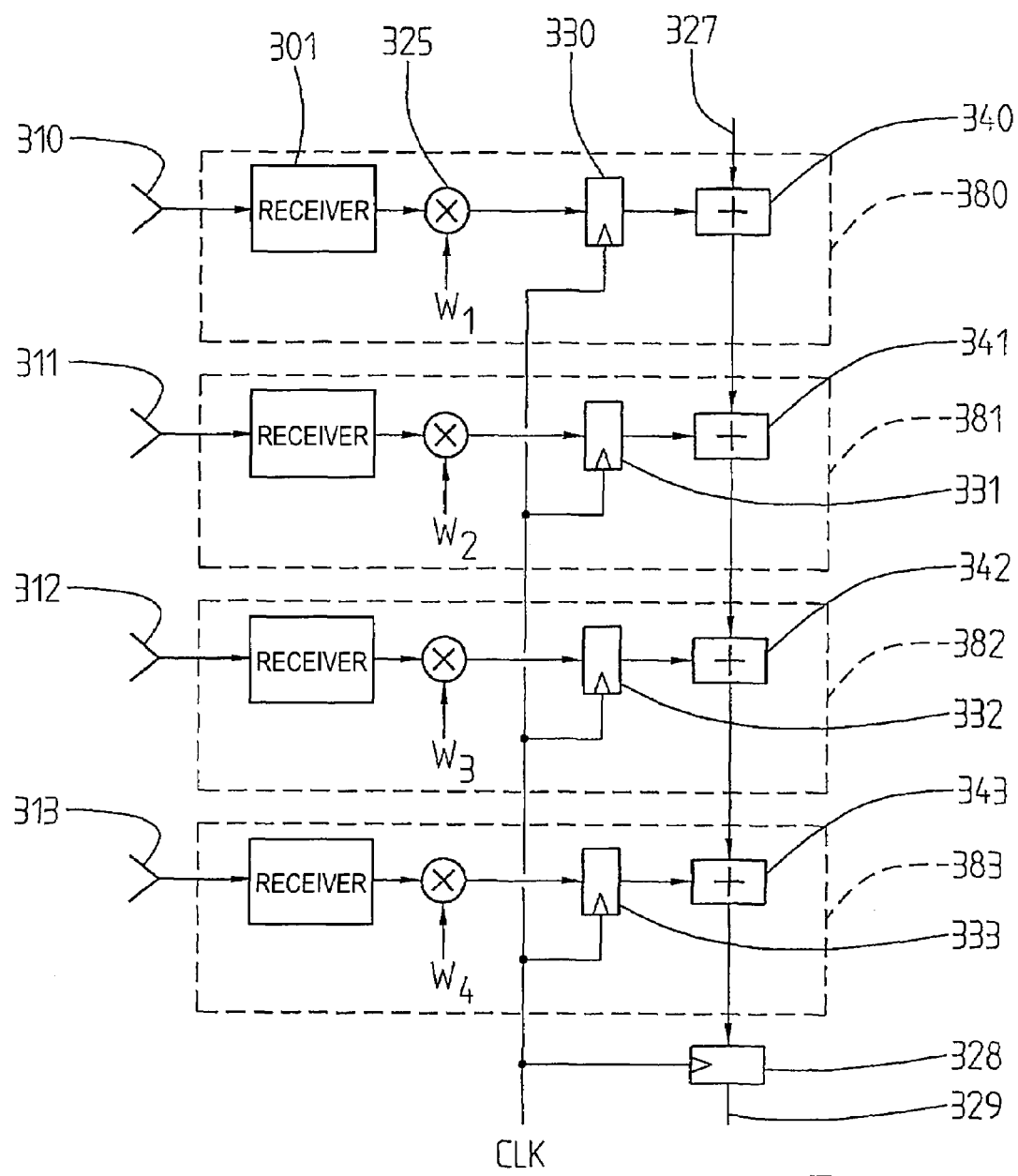
FIG. 3A illustrates an array antenna with improved signal processing associated directly with each separate antenna element.
Figure 3B:
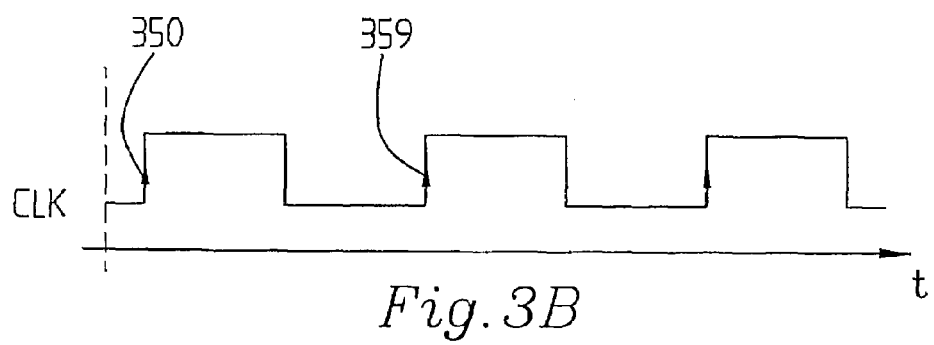
FIG. 3B illustrates a timing diagram for the signal processing of the array antenna system of FIG. 3A.

According to the invention these disadvantages are overcome by the introduction of a serial asynchronous complex adding chain. FIG. 3A illustrates such an array antenna with improved signal processing associated directly with each separate antenna element 310, 311, 312, 313. FIG. 3A illustrates a basic concept of the fully developed invention. Reference is also made to FIG. 3B, which illustrates a timing diagram for the signal processing of the array antenna system of FIG. 3A. As the previously described antenna modules, each antenna module 390, 391, 392, 393 according to FIG. 3A has an antenna element 310, 311, 312, 313 associated to it and further comprises a receiver 301 comprising means for A/D conversion and means for I/Q splitting. Each antenna module 380, 381, 382, 383 further comprises a complex multiplier 325 to multiply the I/Q antenna signal with a respective beam coefficient W1, W2, W3, W4. The results of the multiplications are then latched/stored in multiplier latches 330, 331, 332, 333 at the positive edge 350, 359 of a clock signal CLK.

The latched complex beam element signals are thus, from a positive edge 350, available to a serial asynchronous complex adding chain. The serial asynchronous complex adding chain comprises one complex adder 340, 341, 342, 343 of each antenna module 380, 381, 382, 383. The complex adders 340, 341, 342, 343 are directly coupled together without any intermediate clocked latches for intermediate results. When the latched complex beam element signals and the default value 327 are made available to the adders 340, 341, 342, 343 each adder will add their input values to provide a settled output value. The settling of the output values will ripple down through the adders, i.e. as soon as the first adder 340 in the chain has settled its outputs, the next adder 341 in the chain will soon follow and so on. Then when it is determined that the final adder 343 has settled, i.e. after the settling time of the serial asynchronous complex adding chain, the result of the final adder 343 is latched into a complex beam signal latch 328 to thereby provide a complex beam signal by a positive edge 359 of the clock signal CLK that at the same time latches new values into the multiplier latches 330, 331, 332, 333.

The antenna modules become less complex by not having to have latches that have to have special clock signals. The biggest gain is probably the avoidance of multiphase clock signals that are different to specific antenna modules. According to the invention the antenna modules are the same and require the same clock signals. In this example only a single clock signal CLK is needed that is of the same frequency as the feed of information from the receivers 301, i.e. the A/D converter rate. Throughput is increased as the settling time of the serial asynchronous complex adding chain is less than the time it will take to clock a complex beam signal through the same number of antenna modules as described in relation to FIGS. 2A and 2B. By keeping the antenna modules simple and the same, reliability increases.

It is often desirable to calculate/determine several beams simultaneously. It would not be desirable to have to duplicate all of the antenna modules for each additional beam that is to be determined. However dedicated complex multipliers and adders are available in speeds that are very fast in comparison to desired feed/sample rates, i.e. range resolution. There is also a limit on A/D conversion speed in relation to A/D converter resolution, putting a limit to possible feed/sample rate of an antenna module.

Figure 4A:
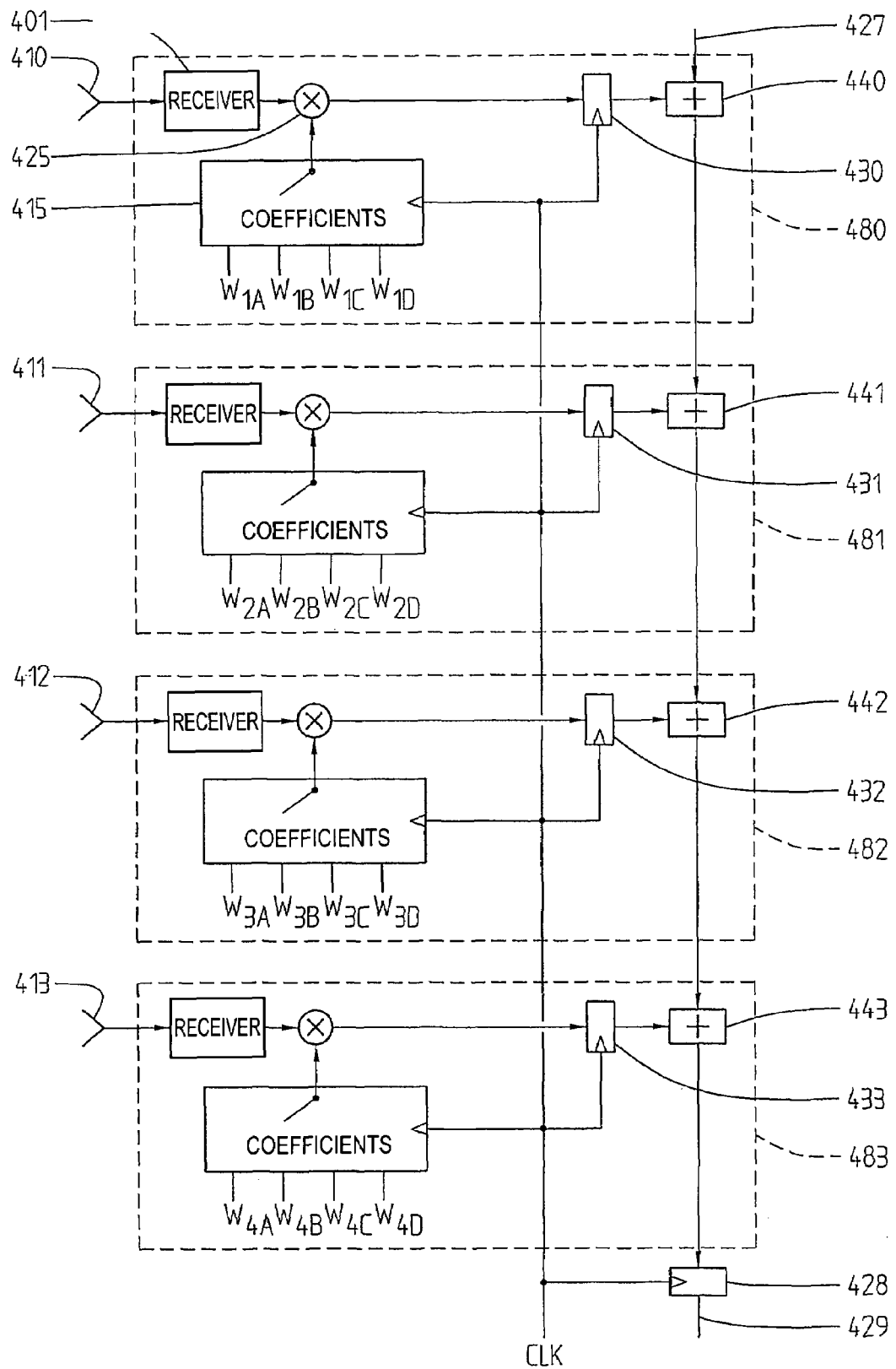
FIG. 4A illustrates an example of an array antenna with improved signal processing with time multiplex.
Figure 4B:
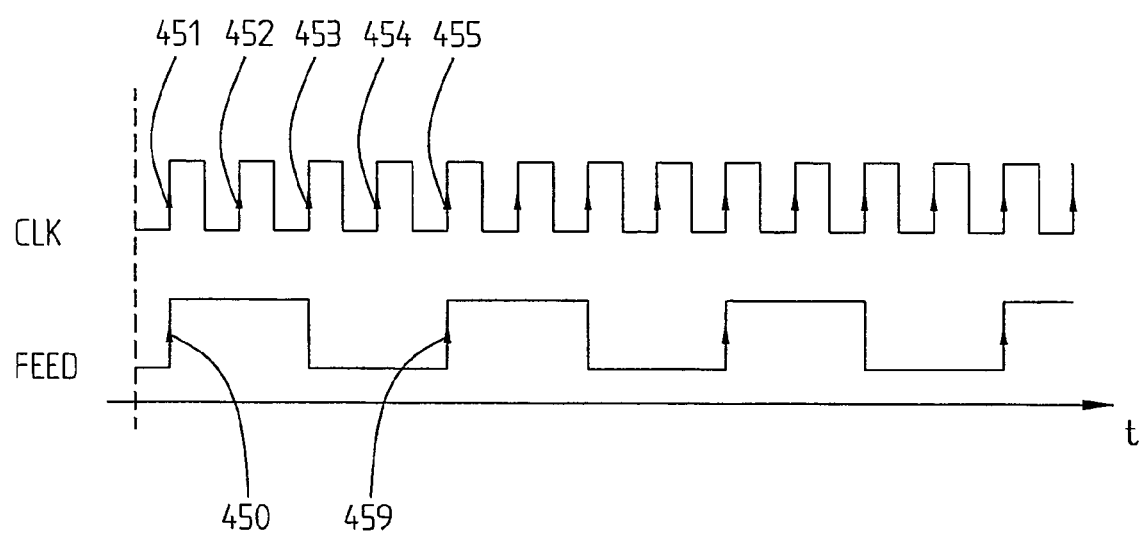
FIG. 4B illustrates a timing diagram for the signal processing of the array antenna system of FIG. 4A.

FIG. 4A illustrates an example of an array antenna with improved signal processing with the ability to calculate four different beams in time multiplex for each sample from the AND converter. Reference will also be made to FIG. 4B, which illustrates a timing diagram for the signal processing of the array antenna system of FIG. 4A. As the antenna modules according to FIG. 3A, the antenna modules 480, 481, 482, 483 according to FIG. 4A have antenna elements 410, 411, 412, 413 associated, receivers 401 comprising A/D converters and I/Q splitters, multipliers 425, multiplier latches 430, 431, 432, 433, and complex adders 440, 441, 442, 443 of the serial asynchronous complex adding chain.

The antenna modules 480, 481, 482, 483 according to FIG. 4A comprises a clock signal controlled coefficient selector 415, which selects one new coefficient for a new beam for each clock signal. This method of providing different coefficients is only an example of how it can be done. Further according to this example four different beams are calculated, each with different coefficients W1A, W1B, W1C, W1D, W2A, W2B, W2C, W2D, W3A, W3B, W3C, W3D, W4A, W4B, W4C, W4D for the different antenna modules 480, 481, 482, 483. The coefficients can suitably be loaded into a memory. The attained four different complex beam signals 429 are time multiplexed on a single serial asynchronous complex adding chain by the use of a clock signal CLK that is four times the sample rate FEED of I/Q antenna signals. During a first rising edge 451 of the clock signal CLK, which coincides with a rising edge 450 of the sample rate FEED, coefficients W1A, W2A, W3A, W4A for a first beam are selected, latching into the multiplier latches 430, 431, 432, 433 the result of coefficients W1D, W2D, W3D, W4D for a fourth beam multiplied with a previous I/Q antenna signal, and the complex beam signal of a third beam of the previous I/Q antenna signal is latched into complex beam signal latch 428. During a second rising edge 452 of the clock signal CLK, coefficients W1B, W2B, W3B, W4B for a second beam are selected, latching into the multiplier latches 430, 431, 432, 433 the result of coefficients W1A, W2A, W3A, W4A for the first beam multiplied with the current I/Q antenna signal, and the complex beam signal of the fourth beam of the previous I/Q antenna signal is latched into complex beam signal latch 428. During a third rising edge 453 of the clock signal CLK, coefficients W1C, W2C, W3C, W4C for a third beam are selected, latching into the multiplier latches 430, 431, 432, 433 the result of coefficients W1B, W2B, W3B, W4B for the second beam multiplied with the current I/Q antenna signal, and the complex beam signal of the first beam of the current I/Q antenna signal is latched into complex beam signal latch 428. During a fourth rising edge 454 of the clock signal CLK, coefficients W1D, W2D, W3D, W4D for a fourth beam are selected, latching into the multiplier latches 430, 431, 432, 433 the result of coefficients W1C, W2C, W3C, W4C for the third beam multiplied with the current I/Q antenna signal, and the complex beam signal of the second beam of the current I/Q antenna signal is latched into complex beam signal latch 428. A fifth rising edge 455 of the clock signal coincides with a new rising edge of the sample rate FEED indicating a new cycle is beginning. Four different beams are thus time multiplexed within a single sample rate FEED period.

To be noted is that all of the antenna modules still only require a single clock signal for the signal processing, this clock signal being the same for all of the antenna modules and having a frequency which corresponds to the rate of calculated beams.

Figure 5:
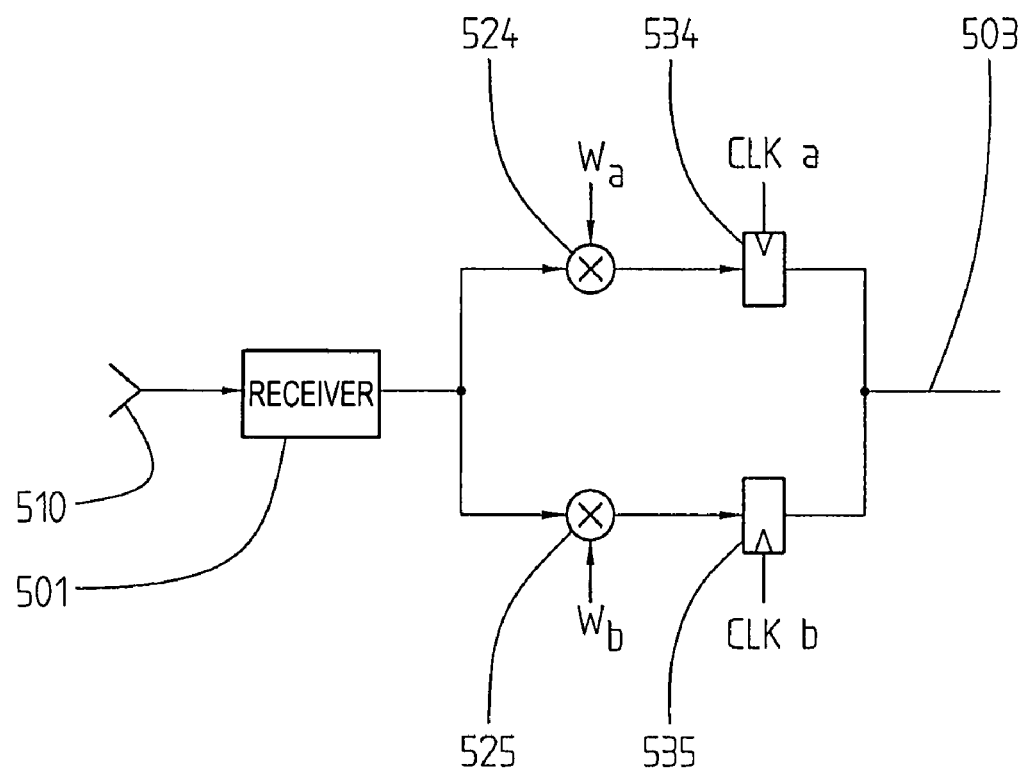
FIG. 5 illustrates an alternative multiplier arrangement, to overcome a relative slowness of used multipliers in relation to used adders in the signal processing.

Depending on the data rates involved and the speed of the complex adders and complex multipliers, there can be bottlenecks due to an available complex adder or complex multiplier not being fast enough for the desired application. FIG. 5 illustrates an alternative multiplier arrangement, to overcome a relative slowness of used complex multipliers in relation to used complex adders in the signal processing. FIG. 5 only illustrates a part of an antenna module associated with an antenna element 510. A receiver 501 comprising an A/D converter and an I/Q splitter will preprocess the electromagnetic signal received by the antenna element for the subsequent signal processing. An I/Q antenna signal from the receiver 501 is fed to, in this example, two complex multipliers 524, 525. Each multiplier 524, 525 multiplies the I/Q antenna signal with a different beam coefficient $W_a$, $W_b$. The results of the multiplications, two different complex beam element signals are latched into respective multiplier latches 534, 535 by respective clock signals CLK a, CLK b. In most applications these will the same clock signal. The latched complex beam element signal 503 can feed a single serial asynchronous complex adder chain as described in relation to FIG. 4A by enabling the multiplier latches 534, 535 alternately, or feed separate serial asynchronous complex adder chains of the type that will be described in relation to FIG. 6A.

Figure 6A:
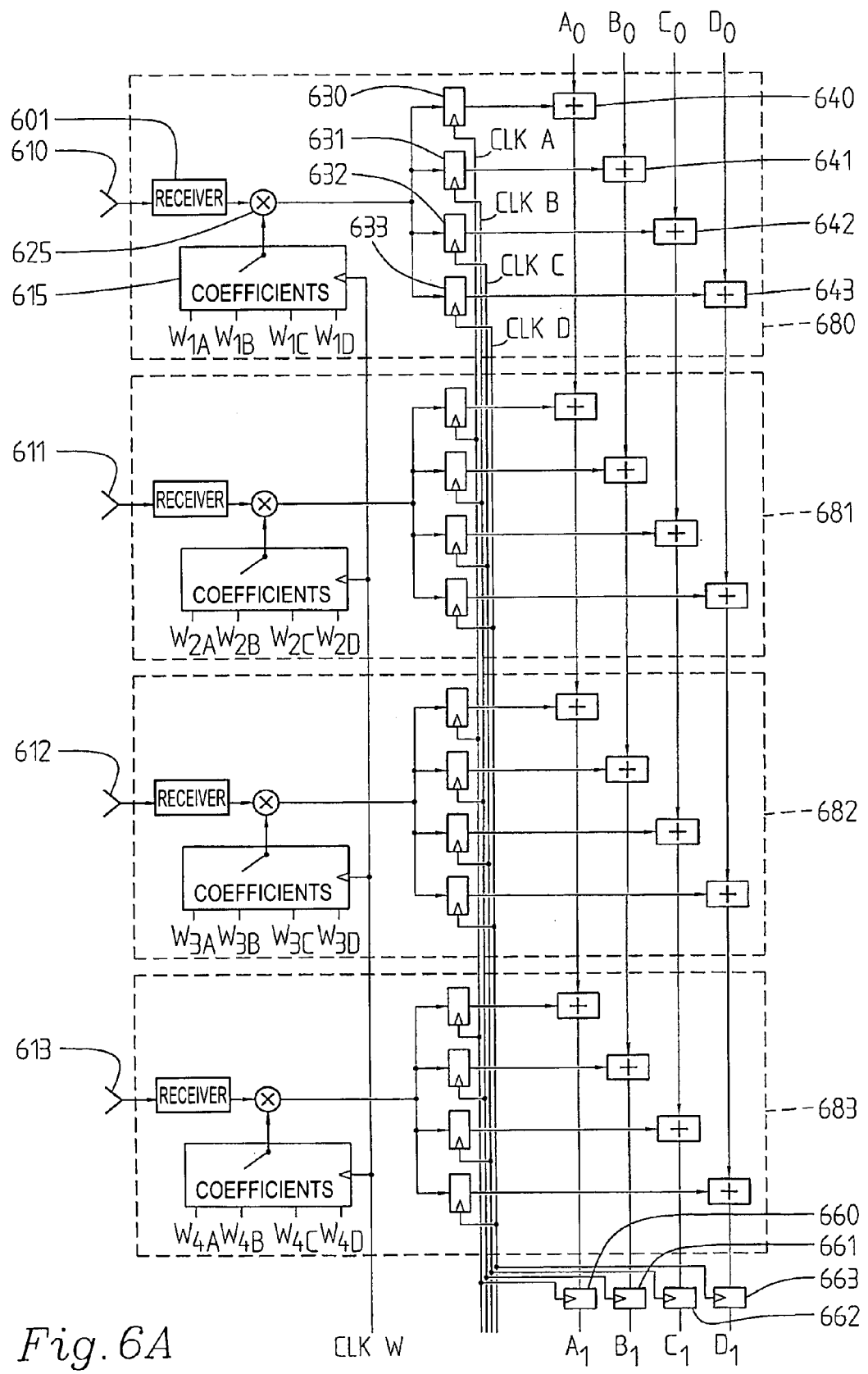
FIG. 6A illustrates an example of an array antenna with improved signal processing with spatial multiplex, i.e. multiple asynchronous adder chains.

FIG. 6A illustrates an example of an array antenna with improved signal processing with spatial multiplex, i.e. multiple serial asynchronous complex adder chains. Such antenna modules 680, 681, 682, 683 can for example be used when the speed of the serial asynchronous complex adding chains cannot meet the demand of a number of desired beams to be calculated per sample interval. The antenna modules 680, 681, 682, 683 are each receiving signals from respective associated antenna elements 610, 611, 612, 613. The antenna modules 680, 681, 682, 683 are further, in this example, equipped with a similar complex multiplier 625 and coefficient selector 615 to those according to FIG. 4A. The antenna modules 680, 681, 682, 683 could be equipped with four complex multipliers instead, the clock signals would of course then be different.

Each of the antenna modules 680, 681, 682, 683 further comprises four multiplier latches 630, 631, 632, 633 each being connected to a complex adder 640, 641, 642, 643. The four complex adders 640, 641, 642, 643 of each antenna module 680, 681, 682, 683 belongs to a separate serial asynchronous complex adder chain, each chain having its own initial value feed $A_0$, $B_0$, $C_0$, $D_0$, its own complex beam signal output $A_1$, $B_1$, $C_1$, $D_1$ latched by a respective complex beam signal latch 660, 661, 662, 663.

Figure 6B:
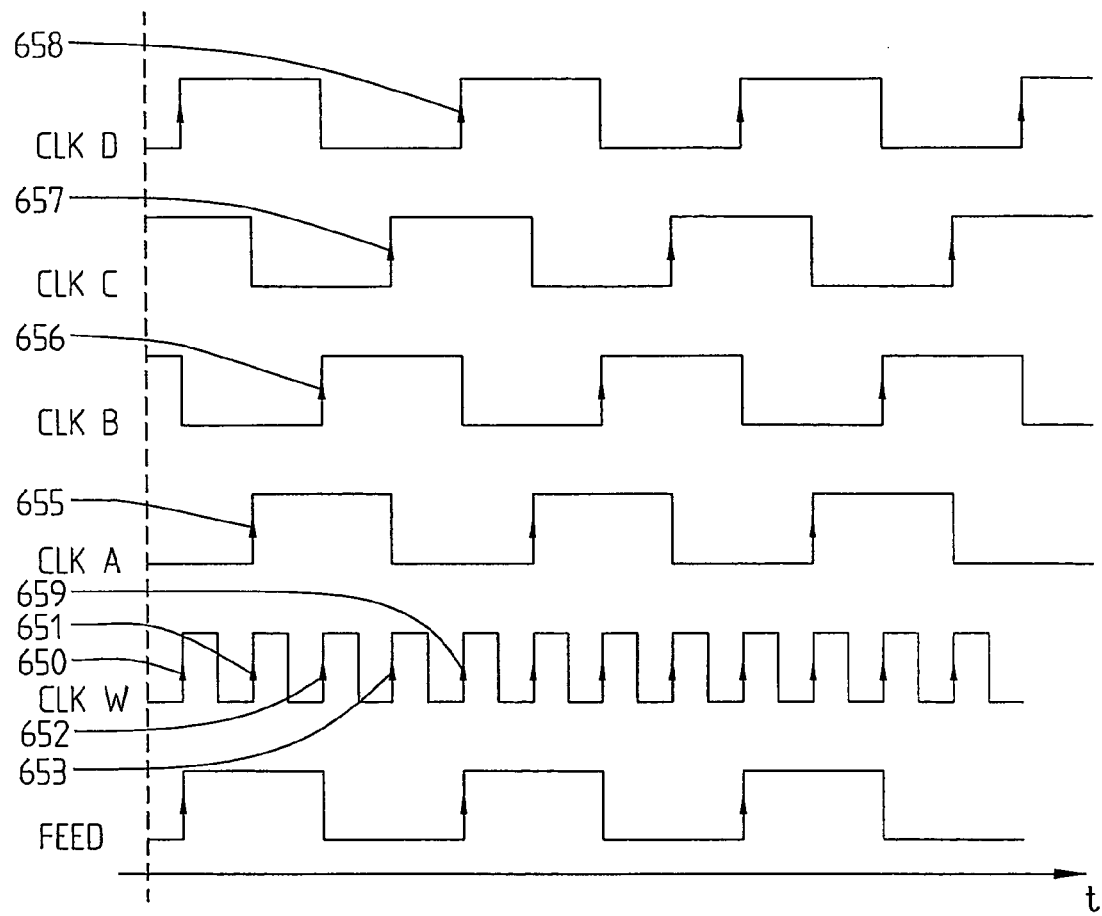
FIG. 6B illustrates a timing diagram for the signal processing of the array antenna system of FIG. 6A.

Reference will now also be made to FIG. 6B, which illustrates a timing diagram for the signal processing of the array antenna system of FIG. 6A. A rising edge 650 of the coefficient clock signal CLK W, selects coefficients W1A, W2A, W3A, W4A for a first beam, for the first asynchronous adder chain, to be multiplied by a current I/Q antenna signal. A second rising edge 651 of the coefficient clock CLK W selects coefficients W1B, W2B, W3B, W4B for a second beam, for the second asynchronous adder chain, to be multiplied by the current I/Q antenna signal. A third rising edge 652 of the coefficient clock signal CLK W, selects coefficients W1C, W2C, W3C, W4C for a third beam, for the third asynchronous adder chain, to be multiplied by the current I/Q antenna signal. A fourth rising edge 653 of the coefficient clock CLK W selects coefficients W1D, W2D, W3D, W4D for a fourth beam, for the fourth asynchronous adder chain, to be multiplied by current I/Q antenna signal. A fifth rising edge 659 of the coefficient clock signal CLK W selects coefficients W1A, W2A, W3A, W4A for the first beam, for the first asynchronous adder chain, to be multiplied by next I/Q antenna signal. The cycle thus repeats. A rising edge 655 of the clock signal of the first asynchronous adder chain CLK A will latch the result of the first beam coefficients W1A, W2A, W3A, W4A multiplied with the current I/Q antenna signal into respective first asynchronous adder chain multiplier latches 630. That rising edge 655 of the clock signal of the first asynchronous adder chain CLK A will also latch a first beam complex beam signal of a previous I/Q antenna signal into the complex beam signal latch of the first asynchronous adder chain 660. A rising edge 656 of the clock signal of the second asynchronous adder chain CLK B will latch the result of the second beam coefficients W1B, W2B, W3B, W4B multiplied with the current I/Q antenna signal into respective second asynchronous adder chain multiplier latches 631. That rising edge 656 of the clock signal of the second asynchronous adder chain CLK B will also latch a second beam complex beam signal of a previous I/Q antenna signal into the complex beam signal latch of the second asynchronous adder chain 661. A rising edge 657 of the clock signal of the third asynchronous adder chain CLK C will latch the result of the third beam coefficients W1C, W2C, W3C, W4C multiplied with the current I/Q antenna signal into respective third asynchronous adder chain multiplier latches 632. That rising edge 657 of the clock signal of the third asynchronous adder chain CLK C will also latch a third beam complex beam signal of a previous I/Q antenna signal into the complex beam signal latch of the third asynchronous adder chain 662. A rising edge 658 of the clock signal of the fourth asynchronous adder chain CLK D will latch the result of the fourth beam coefficients W1D, W2D, W3D, W4D multiplied with the current I/Q antenna signal into respective fourth asynchronous adder chain multiplier latches 633. That rising edge 658 of the clock signal of the fourth asynchronous adder chain CLK D will also latch a fourth beam complex beam signal of a previous I/Q antenna signal into the complex beam signal latch of the fourth asynchronous adder chain 660.

To be noted is that all of the antenna modules still only require the same clock signals CLK A, CLK B, CLK C, CLK D, CLK W for the signal processing, albeit several clock signals in these types of embodiments. Most of the clock signals CLK A, CLK B, CLK C, CLK D being the same rate as the sample rate FEED.

Figure 7:
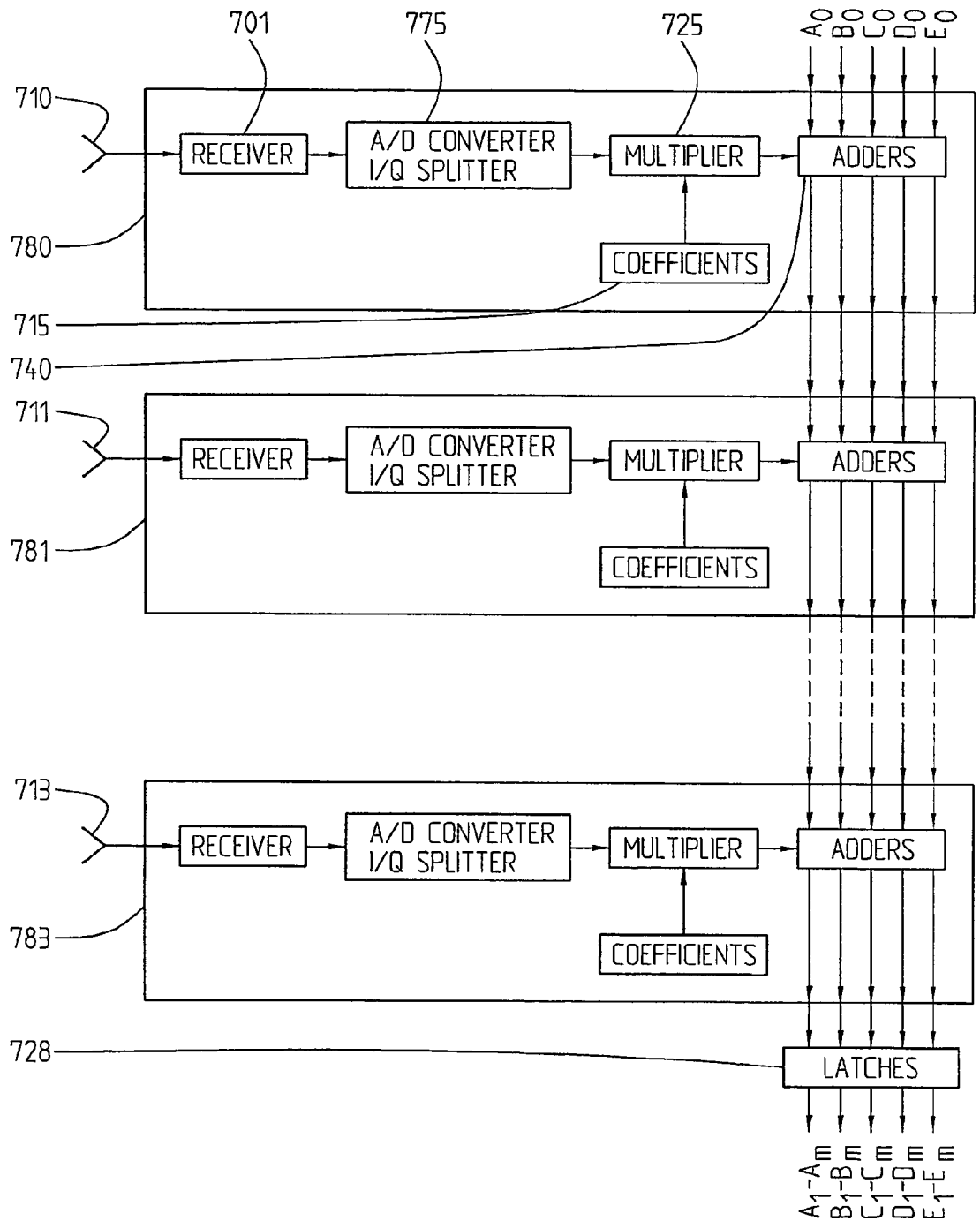
FIG. 7 illustrates a block diagram of an array antenna system with improved signal processing directly associated with each separate antenna element.

Beamforming with spatial multiplex such as described according to FIG. 6A and time multiplexing such as described according to FIG. 4A, can of course be combined. FIG. 7 illustrates a block diagram of such an array antenna system with improved signal processing directly associated with each separate antenna element, comprising beamforming with both spatial and time multiplex. Each of the antenna modules 780, 781, 783 comprise a receiver 701 that transforms electromagnetic signals received by the associated antenna elements 710, 711, 713 to a desirable amplitude and frequency that is suitable for the subsequent A/D and I/Q splitter 775. The antenna modules 780, 781, 783 further comprise one or more complex multipliers 725, a storage for one or more complex coefficients 715 for the different desired beams, and one or more complex adders 740 for the serial asynchronous complex adder chains. An array antenna system will provide initial values $A_0$, $B_0$, $C_0$, $D_0$, $E_0$ for the serial asynchronous adder chains, and have complex beam signal latches 728 for the results of the serial asynchronous adder chains, a plurality of time and spatial multiplexed complex beam signals $A_1$-$A_m$, $B_1$-$B_m$, $C_1$-$C_m$, $D_1$-$D_m$, $E_1$-$E_m$.

Figure 8:
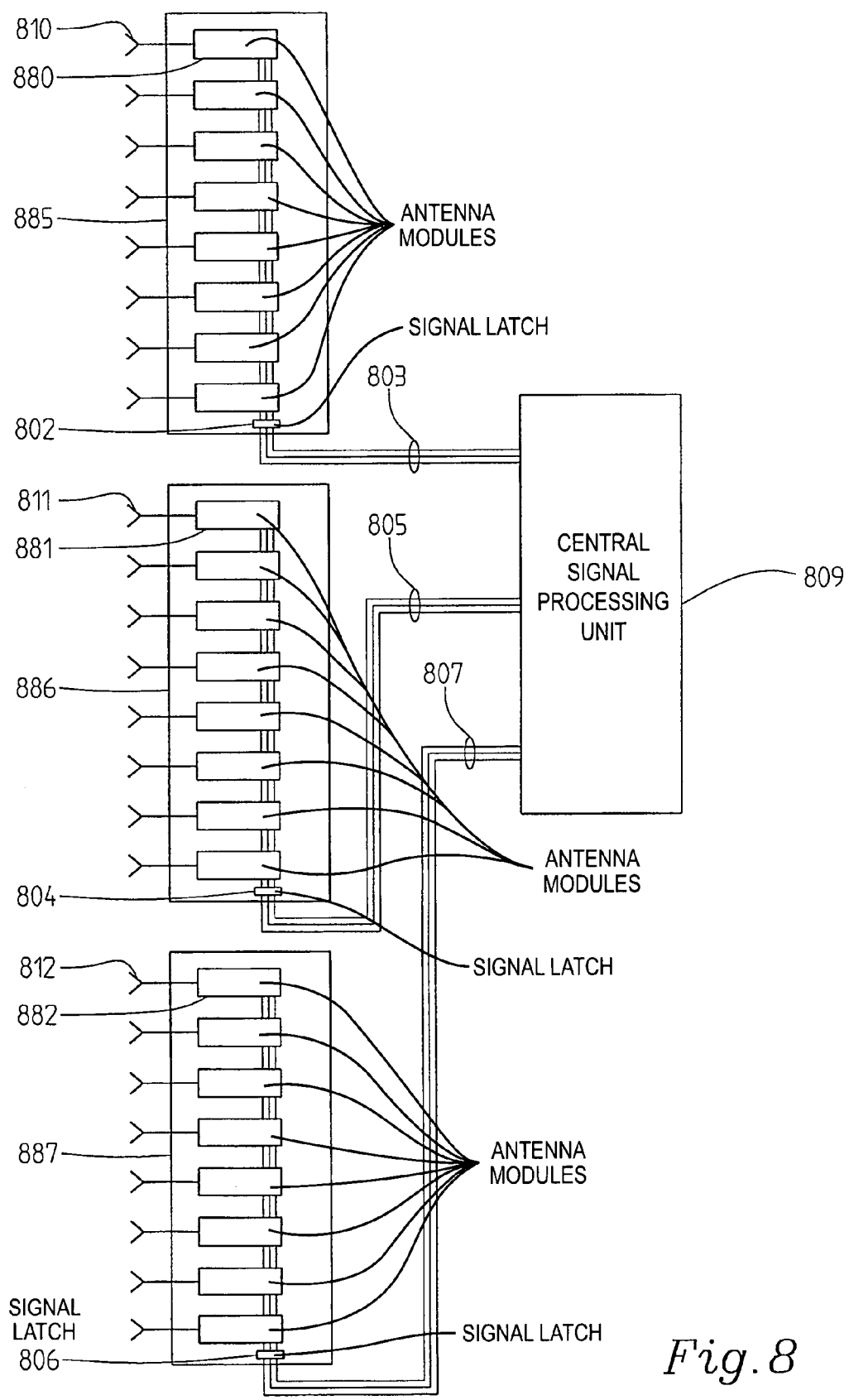
FIG. 8 illustrates a block diagram of an extended array antenna system with improved signal processing directly associated with each separate antenna element.

When the number of antenna elements in an array antenna becomes very large, then the serial asynchronous complex adder chains might become too long. In such a case the serial asynchronous complex adder chains are divided and the sub results fed into a central signal processing unit for final processing. FIG. 8 illustrates a block diagram of an extended array antenna system with improved signal processing directly associated with each separate antenna element with divided serial asynchronous complex adder chains. Illustrated are three array antenna submodules 885, 886, 887, each of which comprise antenna elements 810, 811, 812 and associated antenna modules 880, 881, 882. The serial asynchronous complex adder chains of the array antenna submodules 885, 886, 887 are ended with complex beam signal latches 802, 804, 806 whose values are then fed 803, 805, 807 to a central signal processing unit 809 for final processing.

As a summary, the invention can basically be described as a method and a system, which provides an efficient manner of creating one or more beamformer signals from an array antenna comprising a plurality of antenna elements, each antenna element being associated directly with an antenna module, by the use of a serial asynchronous complex adding chain, distributed among the antenna modules. The invention is not limited to the embodiments described above but may be varied within the scope of the appended patent claims.

FIG. 1 illustrates an example of an array antenna system with a central signal processing unit,
101 a first possible receiver at a corresponding first antenna element,
102 a first connection/cable between the first antenna element, with or without receiver, and a central signal processing unit,
103 a second possible receiver at a corresponding second antenna element,
104 a second connection/cable between the second antenna element, with or without receiver, and the central signal processing unit,
105 a third possible receiver at a corresponding third antenna element,
106 a third connection/cable between the third antenna element, with or without receiver, and the central signal processing unit,
107 a fourth possible receiver at a corresponding fourth antenna element,
108 a fourth connection/cable between the fourth antenna element, with or without receiver, and the central signal processing unit,
109 the central signal processing unit,
110 the first antenna element of an array antenna,
111 the second antenna element of an array antenna,
112 the third antenna element of an array antenna,
113 the fourth antenna element of an array antenna.

FIG. 2A illustrates an example of an array antenna with at least partial signal processing directly associated with each separate antenna element,
201 a receiver, A/D converter and I/Q splitter of a first antenna module,
210 the first antenna element of an array antenna,
211 the second antenna element of an array antenna,
212 the third antenna element of an array antenna,
213 the fourth antenna element of an array antenna,
220 an adder latch of the first antenna module,
221 an adder latch of a second antenna module,
222 an adder latch of a third antenna module,
223 an adder latch of a fourth antenna module,
225 a multiplier of the first antenna module, multiplying the received antenna value with a coefficient W1,
227 default/test entry of adder chain,
229 result of adder chain, complex beam signal,
230 a multiplier latch of the first antenna module,
231 a multiplier latch of the second antenna module,
232 a multiplier latch of the third antenna module,
233 a multiplier latch of the fourth antenna module,
240 an adder of the first antenna module, adding the default value with the multiplier latched value, the result being stored in the adder latch of the first antenna module,
241 an adder of the second antenna module, adding the value of the adder latch of the first antenna module with the multiplier latched value, the result being stored in the adder latch of the second antenna module,
242 an adder of the third antenna module, adding the value of the adder latch of the second antenna module with the multiplier latched value, the result being stored in the adder latch of the third antenna module,
243 an adder of the fourth antenna module, adding the value of the adder latch of the third antenna module with the multiplier latched value, the result being stored in the adder latch of the fourth antenna module,
271 I/Q antenna signal,
273 I/Q antenna signal multiplied with a coefficient W1,
290 the first antenna module,
291 the second antenna module,
292 the third antenna module,
293 the fourth antenna module,
CLK A1 clock signal for loading the adder latch of the first antenna module,
CLK A2 clock signal for loading the adder latch of the second antenna module,
CLK A3 clock signal for loading the adder latch of the third antenna module,
CLK A4 clock signal for loading the adder latch of the fourth antenna module,
CLK L clock signal for loading the multiplier latches of all of the antenna modules,
W1 coefficient value of the first antenna module for a desired beam,
W2 coefficient value of the second antenna module for a desired beam,
W3 coefficient value of the third antenna module for a desired beam,
W4 coefficient value of the fourth antenna module for a desired beam.

Figure 2B:
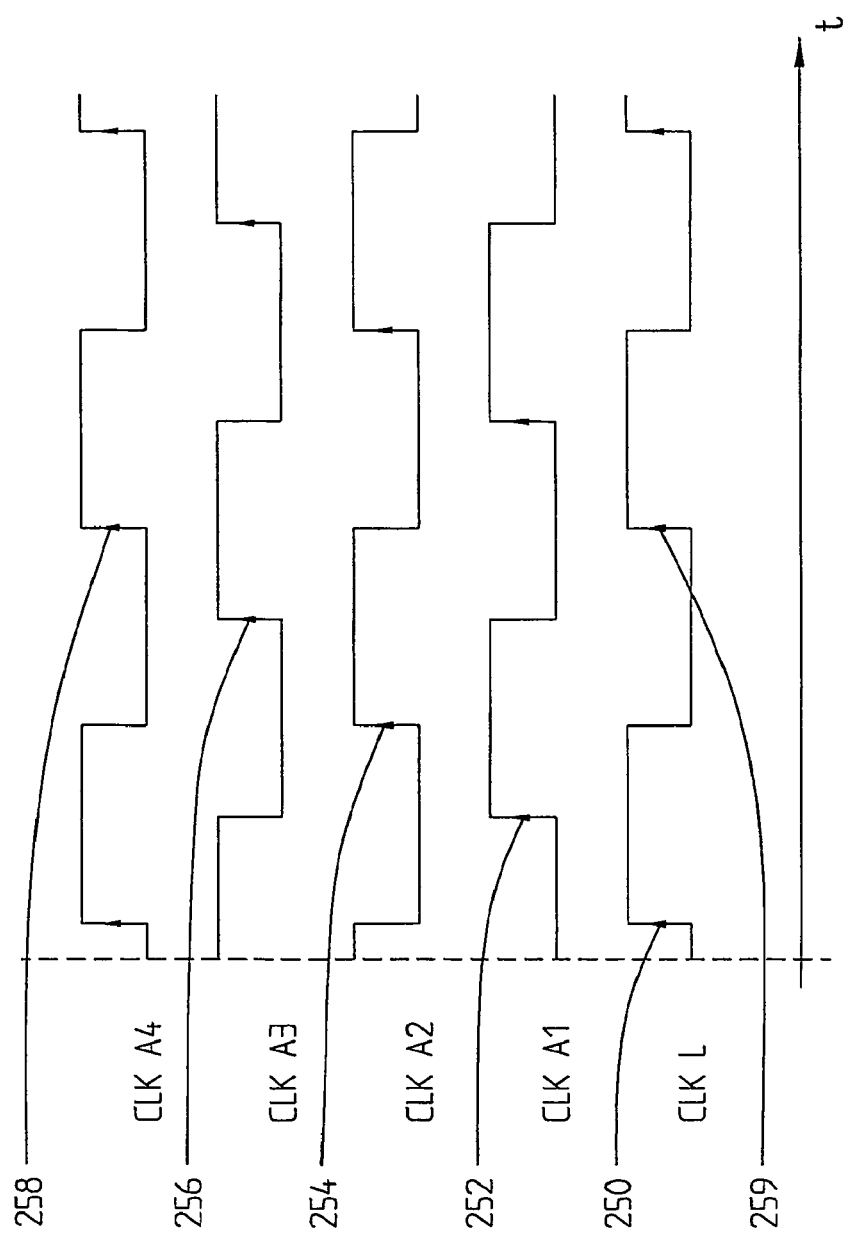
FIG. 2B illustrates a timing diagram for the array antenna system according to FIG. 2A.

FIG. 2B illustrates a timing diagram for the array antenna system according to FIG. 2A, 250 rising edge of multiplier latches' clock signal, which loads an I/Q antenna signal multiplied with a coefficient into the corresponding multiplier latches, 252 rising edge of the clock signal for loading the adder latch of the first antenna module, the adder of the first antenna module is finished adding, 254 rising edge of the clock signal for loading the adder latch of the second antenna module, the adder of the second antenna module is finished adding, 256 rising edge of the clock signal for loading the adder latch of the third antenna module, the adder of the third antenna module is finished adding, 258 rising edge of the clock signal for loading the adder latch of the fourth antenna module, the adder of the fourth antenna module is finished adding, 259 rising edge of clock signal of the multiplier latches, indicating a new cycle beginning, CLK A1 clock signal for loading the adder latch of the first antenna module, CLK A2 clock signal for loading the adder latch of the second antenna module, CLK A3 clock signal for loading the adder latch of the third antenna module, CLK A4 clock signal for loading the adder latch of the fourth antenna module, CLK L clock signal for loading the multiplier latches of all of the antenna modules.

FIG. 3A illustrates an array antenna with improved signal processing associated directly with each separate antenna element, 301 a receiver, A/D converter and I/Q splitter of a first antenna module, 310 the first antenna element of an array antenna,
311 the second antenna element of an array antenna,
312 the third antenna element of an array antenna,
313 the fourth antenna element of an array antenna,
325 a multiplier of the first antenna module, multiplying the received antenna value with a coefficient W1,
327 default/test entry of adder chain,
328 complex beam signal latch,
329 result of adder chain, complex beam signal
330 a multiplier latch of the first antenna module,
331 a multiplier latch of the second antenna module,
332 a multiplier latch of the third antenna module,
333 a multiplier latch of the fourth antenna module,
340 an adder of the first antenna module, adding the default value with the multiplier latched value, the result being fed to an adder of the second antenna module,
341 the adder of the second antenna module, adding the value of the adder of the first antenna module with the multiplier latched value, the result being fed to an adder of the third antenna module,
342 the adder of the third antenna module, adding the value of the adder of the second antenna module with the multiplier latched value, the result being fed to an adder of the fourth antenna module,
343 the adder of the fourth antenna module, adding the value of the adder of the third antenna module with the multiplier latched value, the result being fed to complex beam signal latch,
380 the first antenna module,
381 the second antenna module,
382 the third antenna module,
383 the fourth antenna module,
CLK clock signal for loading the multiplier latches of all of the antenna modules and for loading a complex beam signal from the complete adder chain, W1 coefficient value of the first antenna module for a desired beam,
W2 coefficient value of the second antenna module for a desired beam,
W3 coefficient value of the third antenna module for a desired beam,
W4 coefficient value of the fourth antenna module for a desired beam.

FIG. 3B illustrates a timing diagram for the signal processing of the array antenna system of FIG. 3A, 350 rising edge of multiplier latches' clock signal, which loads an I/Q antenna signal multiplied with a coefficient into the corresponding multiplier latches, and loads the complex beam signal into a latch from the asynchronous adding chain, 359 rising edge of clock signal indicating a new cycle beginning, CLK clock signal for loading the multiplier latches of all of the antenna modules and for loading a complex beam signal from the complete asynchronous adding chain.

FIG. 4A illustrates an example of an array antenna with improved signal processing with time multiplex, 401 a receiver, A/D converter and I/Q splitter of a first antenna module,
410 the first antenna element of an array antenna,
411 the second antenna element of an array antenna,
412 the third antenna element of an array antenna,
413 the fourth antenna element of an array antenna,
415 clock signal controlled coefficient selector,
425 a multiplier of the first antenna module, multiplying the received antenna value with a coefficient,
427 default/test entry of adder chain,
428 complex beam signal latch,
429 result of adder chain, complex beam signal
430 a multiplier latch of the first antenna module,
431 a multiplier latch of the second antenna module,
432 a multiplier latch of the third antenna module,
433 a multiplier latch of the fourth antenna module,
440 an adder of the first antenna module, adding the default value with the multiplier latched value, the result being fed to an adder of the second antenna module,
441 the adder of the second antenna module, adding the value of the adder of the first antenna module with the multiplier latched value, the result being fed to an adder of the third antenna module,
442 the adder of the third antenna module, adding the value of the adder of the second antenna module with the multiplier latched value, the result being fed to an adder of the fourth antenna module,
443 the adder of the fourth antenna module, adding the value of the adder of the third antenna module with the multiplier latched value, the result being fed to complex beam signal latch,
480 the first antenna module,
481 the second antenna module,
482 the third antenna module,
483 the fourth antenna module,
CLK clock signal for loading the multiplier latches of all of the antenna modules and for loading a complex beam signal from the complete adder chain,
W1A coefficient value of the first antenna module for a first desired beam,
W1B coefficient value of the first antenna module for a second desired beam,
W1C coefficient value of the first antenna module for a third desired beam, W1D coefficient value of the first antenna module for a fourth desired beam, W2A coefficient value of the second antenna module for the first desired beam, W2B coefficient value of the second antenna module for the second desired beam, W2C coefficient value of the second antenna module for the third desired beam, W2D coefficient value of the second antenna module for the fourth desired beam, W3A coefficient value of the third antenna module for the first desired beam, W3B coefficient value of the third antenna module for the second desired beam, W3C coefficient value of the third antenna module for third desired beam, W3D coefficient value of the third antenna module for the fourth desired beam, W4A coefficient value of the fourth antenna module for the first desired beam, W4B coefficient value of the fourth antenna module for the second desired beam, W4C coefficient value of the fourth antenna module for the third desired beam, W4D coefficient value of the fourth antenna module for the fourth desired beam.

FIG. 4B illustrates a timing diagram for the signal processing of the array antenna system of FIG. 4A, 450 rising edge of feed supplying a current antenna signal value, 451 rising edge of clock signal, which loads an I/Q antenna signal multiplied with a coefficient into the corresponding multiplier latches, and loads the complex beam signal into a latch from the asynchronous adding chain, and selects a new coefficient for a new beam, W1A, W2A, W3A, and W4A selected, W1D, W2D, W3D, and W4D multiplied with previous I/Q antenna signal loaded into respective multiplier latches, W1C, W2C, W3C, and W4C complex beam signal of previous I/Q antenna signal loaded into latch, 452 W1B, W2B, W3B, and W4B selected, W1A, W2A, W3A, and W4A multiplied with current I/Q antenna signal loaded into respective multiplier latches, W1D, W2D, W3D, and W4D complex beam signal of previous I/Q antenna signal loaded into latch, 453 W1C, W2C, W3C, and W4C selected, W1B, W2B, W3B, and W4B multiplied with current I/Q antenna signal loaded into respective multiplier latches, W1A, W2A, W3A, and W4A complex beam signal of current I/Q antenna signal loaded into latch, 454 W1D, W2D, W3D, and W4D selected, W1C, W2C, W3C, and W4C multiplied with current I/Q antenna signal loaded into respective multiplier latches, W1B, W2B, W3B, and W4B complex beam signal of current I/Q antenna signal loaded into latch, 455 W1A, W2A, W3A, and W4A selected, W1D, W2D, W3D, and W4D multiplied with current I/Q antenna signal loaded into respective multiplier latches, W1C, W2C, W3C, and W4C complex beam signal of current I/Q antenna signal loaded into latch, 459 rising edge of clock signal indicating a new cycle beginning, supplying a next antenna signal value, CLK clock signal for loading the multiplier latches of all of the antenna modules and for loading a complex beam signal from the complete asynchronous adding chain, a multiple of the feed rate, thus computing several beams, FEED feed rate/update rate of the A/D converter.

FIG. 5 illustrates an alternative multiplier arrangement, to overcome a relative slowness of used multipliers in relation to used adders in the signal processing, 501 a receiver, A/D converter and I/Q splitter, 503 signal to the asynchronous adder chain, 510 antenna element, 524 a first multiplier, multiplying the received antenna value with a coefficient Wb, 525 a second multiplier, multiplying the received antenna value with a coefficient Wa, 534 a first multiplier latch associated with the first multiplier, 535 a second multiplier latch associated with the second multiplier, CLKa first clock signal, CLKb second clock signal, Wa first coefficient, Wb second coefficient.

FIG. 6A illustrates an example of an array antenna with improved signal processing with spatial multiplex, i.e. multiple asynchronous adder chains, 601 a receiver, A/D converter and I/Q splitter of a first antenna module, 610 the first antenna element of an array antenna, 611 the second antenna element of an array antenna, 612 the third antenna element of an array antenna, 513 the fourth antenna element of an array antenna, 615 clock signal controlled coefficient selector, 625 a multiplier of the first antenna module, multiplying the received antenna value with a coefficient, 630 a multiplier latch of a first asynchronous adder chain, of a first antenna module, 631 a multiplier latch of a second asynchronous adder chain, of the first antenna module, 632 a multiplier latch of a third asynchronous adder chain, of the first antenna module, 633 a multiplier latch of the fourth asynchronous adder chain, of the first antenna module, 640 an adder of the first asynchronous adder chain of the first antenna module, adding a default value with the multiplier latched value of the first asynchronous adder chain, the result being fed to an adder of the first asynchronous adder chain of the second antenna module, 641 an adder of the second asynchronous adder chain of the first antenna module, adding a default value with the multiplier latched value of the second asynchronous adder chain, the result being fed to an adder of the second asynchronous adder chain of the second antenna module, 642 an adder of the third asynchronous adder chain of the first antenna module, adding a default value with the multiplier latched value of the third asynchronous adder chain, the result being fed to an adder of the third asynchronous adder chain of the second antenna module, 643 an adder of the fourth asynchronous adder chain of the first antenna module, adding a default value with the multiplier latched value of the fourth asynchronous adder chain, the result being fed to an adder of the fourth asynchronous adder chain of the second antenna module, 660 complex beam signal latch of first asynchronous adder chain, 661 complex beam signal latch of second asynchronous adder chain, 662 complex beam signal latch of third asynchronous adder chain, 663 complex beam signal latch of fourth asynchronous adder chain, 680 the first antenna module, 681 the second antenna module,
682 the third antenna module,
683 the fourth antenna module,
$A_0$ default/test entry of first asynchronous adder chain,
$A_1$ result of first asynchronous adder chain, a first complex beam signal,
$B_0$ default/test entry of second asynchronous adder chain,
$B_1$ result of second asynchronous adder chain, a second complex beam signal,
$C_0$ default/test entry of third asynchronous adder chain,
$C_1$ result of third asynchronous adder chain, a third complex beam signal,
$D_0$ default/test entry of fourth asynchronous adder chain,
$D_1$ result of fourth asynchronous adder chain, a fourth complex beam signal,
CLK A clock signal for loading the multiplier latches of the first asynchronous adder chain of all of the antenna modules and for loading the first complex beam signal from the complete first asynchronous adder chain,
CLK B clock signal for loading the multiplier latches of the second asynchronous adder chain of all of the antenna modules and for loading the second complex beam signal from the complete second asynchronous adder chain,
CLK C clock signal for loading the multiplier latches of the third asynchronous adder chain of all of the antenna modules and for loading the third complex beam signal from the complete third asynchronous adder chain,
CLK D clock signal for loading the multiplier latches of the fourth asynchronous adder chain of all of the antenna modules and for loading the fourth complex beam signal from the complete fourth asynchronous adder chain,
CLK W clock signal for the coefficient selector,
W1A coefficient value of the first antenna module for a first desired beam,
W1B coefficient value of the first antenna module for a second desired beam,
W1C coefficient value of the first antenna module for a third desired beam,
W1D coefficient value of the first antenna module for a fourth desired beam,
W2A coefficient value of the second antenna module for the first desired beam,
W2B coefficient value of the second antenna module for the second desired beam,
W2C coefficient value of the second antenna module for the third desired beam,
W2D coefficient value of the second antenna module for the fourth desired beam,
W3A coefficient value of the third antenna module for the first desired beam,
W3B coefficient value of the third antenna module for the second desired beam,
W3C coefficient value of the third antenna module for third desired beam,
W3D coefficient value of the third antenna module for the fourth desired beam,
W4A coefficient value of the fourth antenna module for the first desired beam,
W4B coefficient value of the fourth antenna module for the second desired beam,
W4C coefficient value of the fourth antenna module for the third desired beam,
W4D coefficient value of the fourth antenna module for the fourth desired beam.

FIG. 6B illustrates a timing diagram for the signal processing of the array antenna system of FIG. 6A, 650 rising edge of coefficient clock signal, which selects a new coefficient for a new beam, W1A, W2A, W3A, and W4A for the first asynchronous adder chain selected to be multiplied by current I/Q antenna signal,
651 W1B, W2B, W3B, and W4B for the second asynchronous adder chain selected to be multiplied by current I/Q antenna signal,
652 W1C, W2C, W3C, and W4C for the third asynchronous adder chain selected to be multiplied by current I/Q antenna signal,
653 W1D, W2D, W3D, and W4D for the fourth asynchronous adder chain selected to be multiplied by current I/Q antenna signal,
655 W1A, W2A, W3A, and W4A multiplied with current I/Q antenna signal loaded into respective first asynchronous adder chain multiplier latches, and the first complex beam signal of previous I/Q antenna signal loaded into latch,
656 W1B, W2B, W3B, and W4B multiplied with current I/Q antenna signal loaded into respective second asynchronous adder chain multiplier latches, and the second complex beam signal of previous I/Q antenna signal loaded into latch,
657 W1C, W2C, W3C, and W4C multiplied with current I/Q antenna signal loaded into respective third asynchronous adder chain multiplier latches, and the third complex beam signal of previous I/Q antenna signal loaded into latch,
658 W1D, W2D, W3D, and W4D multiplied with current I/Q antenna signal loaded into respective fourth asynchronous adder chain multiplier latches, and the fourth complex beam signal of previous I/Q antenna signal loaded into latch,
659 W1A, W2A, W3A, and W4A selected to be multiplied by next I/Q antenna signal,
CLK A clock signal for loading the multiplier latches of the first asynchronous adder chain of all of the antenna modules and for loading the first complex beam signal from the complete first asynchronous adder chain,
CLK B clock signal for loading the multiplier latches of the second asynchronous adder chain of all of the antenna modules and for loading the second complex beam signal from the complete second asynchronous adder chain,
CLK C clock signal for loading the multiplier latches of the third asynchronous adder chain of all of the antenna modules and for loading the third complex beam signal from the complete third asynchronous adder chain,
CLK D clock signal for loading the multiplier latches of the fourth asynchronous adder chain of all of the antenna modules and for loading the fourth complex beam signal from the complete fourth asynchronous adder chain,
CLK W clock signal for the coefficient selector,
FEED feed rate/update rate of the A/D converter, rising edge of feed supplying a current I/Q antenna signal value.

FIG. 7 illustrates a block diagram of an array antenna system with improved signal processing directly associated with each separate antenna element, 701 a receiver of a first antenna module,
710 the first antenna element of an array antenna,
711 the second antenna element of an array antenna,
712 the third antenna element of an array antenna,
713 the fourth antenna element of an array antenna,
715 coefficient supply,
725 a multiplier of the first antenna module, multiplying the received antenna value with a coefficient,
728 complex beam signal latches, 740 an adder of the first asynchronous adder chains of the first antenna module, adding default values with the multiplier latched values of respective asynchronous adder chain, the results being fed to an adder of the respective asynchronous adder chain of the second antenna module, 775 A/D converter and I/Q splitter of the first antenna module, 780 the first antenna module, 781 the second antenna module, 783 the n:th antenna module, $A_0$ default/test entry of first asynchronous adder chain, $A_1$-$A_m$ result of first asynchronous adder chain, a plurality of time multiplexed complex beam signals, $B_0$ default/test entry of second asynchronous adder chain, $B_1$-$B_m$ result of second asynchronous adder chain, a plurality of time multiplexed complex beam signals, $C_0$ default/test entry of third asynchronous adder chain, $C_1$-$C_m$ result of third asynchronous adder chain, a plurality of time multiplexed complex beam signals, $D_0$ default/test entry of fourth asynchronous adder chain, $D_1$-$D_m$ result of fourth asynchronous adder chain, a plurality of time multiplexed complex beam signals, $E_0$ default/test entry of fifth asynchronous adder chain, $E_1$-$E_m$ result of fifth asynchronous adder chain, a plurality of time multiplexed complex beam signals.

FIG. 8 illustrates a block diagram of an extended array antenna system with improved signal processing directly associated with each separate antenna element, 802 complex beam signal latches of a first array antenna submodule, 803 a connection/cable between the first array antenna submodule and a central processing unit, 804 complex beam signal latches of a second array antenna submodule, 805 a connection/cable between the second array antenna submodule and the central processing unit, 806 complex beam signal latches of an n:th array antenna submodule, 807 a connection/cable between the n:th array antenna submodule and the central processing unit, 809 the central processing unit, 810 an antenna element of the first array antenna submodule, 811 an antenna element of the second array antenna submodule, 812 an antenna element of the n:th array antenna submodule, 880 an antenna module of the first array antenna submodule, 881 an antenna module of the second array antenna submodule, 882 an antenna module of the n:th array antenna submodule, 885 the first array antenna submodule, 886 the second array antenna submodule, 887 the n:th array antenna submodule.

The invention claimed is:

1. A method of producing a digital beamformer signal using output signals generated by an array of antenna elements in response to the reception of electromagnetic waves, where each antenna element is directly associated with an antenna module, each of which processes an output signal generated by a corresponding antenna element characterized in that the method comprises the steps of:

each antenna module providing a working frequency signal from the output signal generated by the corresponding associated antenna element;

each antenna module converting the working frequency signal to a complex digital antenna signal at a first data rate;

each antenna module multiplying the complex digital antenna signal with a complex beam coefficient generating a complex beam element signal at a second data rate;

asynchronously adding the generated complex beam element signals in groups comprising at least two antenna modules forming a complex beam signal by means of complex adders on the respective antenna modules being intercoupled to form respective serial asynchronous complex adding chains;

providing the digital beamformer signal from the complex beam signal.

2. The method according to claim 1, characterized in that the first data rate and the second data rate are the same.

3. The method according to claim 1, characterized in that the second data rate is a multiple of the first data rate, and in that the method further comprises the step of:

in each antenna module changing the complex beam coefficient in pace with the second data rate to thereby at the first data rate generate a multiple of complex beam signals, each of which represents a predetermined beam.

4. The method according to claim 3, characterized in that the multiple of complex beam signals are time multiplexed on the serial asynchronous complex adding chains.

5. The method according to claim 3, characterized in that each antenna module comprises further complex adders forming multiple serial asynchronous complex adding chains associated with each antenna module, the multiple of complex beam signals being spatially multiplexed on the multiple of serial asynchronous complex adding chains.

6. The method according to claim 3, characterized in that each antenna module comprises further adders forming multiple serial asynchronous complex adding chains associated with each antenna module, the multiple of complex beam signals being both spatially and time multiplexed on the multiple of serial asynchronous complex adding chains.

7. The method according claim 1, characterized in that in the step of asynchronously adding the generated complex beam element signals, adding is performed on a group comprising all antenna modules.

8. The method according claim 1, characterized in that in the step of asynchronously adding the generated complex beam element signals in groups, the antenna modules are divided into at least two groups, and in that the step of providing the digital beamformer signal from the complex beam signal, additionally determines the complex beam signal from the digital beamformer signal of each group serial asynchronous complex adding chain.

9. An array antenna comprising at least two antenna elements arranged for reception of electromagnetic waves, and comprising a beamformer arranged to form at least one reception beam characterized in that at least a part of the beamformer is directly associated with a respective antenna element, each part of the beamformer being directly associated with an antenna element forms an antenna element module of that antenna element, where an antenna element module comprises:

a receiver arranged to provide a working frequency signal;

an analog to digital converter and I/Q splitter arranged to transform the working frequency signal from the receiver into I and Q digital complex signals at a first data rate;

a multiplier arranged to multiply the complex digital I and Q signals with a complex beam coefficient forming a complex beam element signal at a second data rate;

an element latch arranged to freeze the complex beam element signal by a clock signal to form a latched complex beam element signal;

an asynchronous complex adder arranged to add the latched complex beam element signal with an input complex part beam signal, forming an output complex part beam signal;

and in that the output part beam signals of one antenna element module is coupled to the input complex part beam signal of a further antenna element module thus forming a serial asynchronous summing path of the latched complex beam element signals of the antenna element modules generating a complex beam signal.

10. The array antenna according to claim 9, characterized in that the antenna further comprises a beam latch arranged to store the complex beam signal by the clock signal, the element latch and the beam latch are both clocked at the same time.

11. The array antenna according to claim 10, characterized in that the element latch and the beam latch are clocked at the first data rate.

12. The array antenna according to claim 10, characterized in that the element latch and the beam latch are clocked at the second data rate, the second data rate being a multiple of the first data rate, and in that the complex beam coefficient is changed in pace with the second data rate to thereby at the first data rate generate a multiple of complex beam signals, each of which represents a predetermined beam.

13. The array antenna according to claim 12, characterized in that the multiple of complex beam signals are time multiplexed on the serial asynchronous summing path.

14. The array antenna according to claim 10, characterized in that the second data rate is a multiple of the first data rate, and in that the complex beam coefficient is changed in pace with the second data rate to thereby at the first data rate generate a multiple of complex beam element signals, each of which represents a predetermined beam, and in that each of the antenna element modules further comprises:

one or more additional element latches arranged to freeze a complex beam element signal by a clock signal to form one or more additional latched complex beam element signals at a third data rate;

one or more additional asynchronous complex adders each arranged to add one of the one or more additional latched complex beam element signal with an input complex part beam signal, each forming an additional output complex part beam signal; and in that each additional output part beam signal of one antenna element module is coupled to a corresponding additional input complex part beam signal of a further antenna element module thus forming one or more additional serial asynchronous summing paths of the one or more additional latched complex beam element signals of the antenna element modules generating one or more additional complex beam signals, and in that the antenna further comprises one additional beam latch for each additional serial asynchronous summing path, each additional beam latch being arranged to store the additional complex beam signal by the clock signal, the one or more additional element latches and the one or more beam latches are clocked at the same time.

15. The array antenna according to claim 14, characterized in that the third data rate is the same as the first data rate, thus each corresponding element latch and beam latch are clocked at the first data rate and all the complex beam signals are spatially multiplexed on the serial asynchronous summing path and on the one or more additional serial asynchronous summing paths.

16. The array antenna according to claim 14, characterized in that the third data rate is a multiple of the second data rate and in that the element latch and the beam latch are clocked at the third data rate, all the multiple of complex beam signals thus being both spatially and time multiplexed on all the serial asynchronous summing paths.

17. The array antenna according to claim 9, characterized in that all of the antenna element modules of the array antenna are comprised in all of the serial asynchronous summing paths.

18. The array antenna according claim 9, characterized in that the antenna element modules of the array antenna are divided into at least two groups, each group having separate serial asynchronous summing paths, the complex beam signals being fed into a central beamformer part for final computation of the corresponding beams.

* * * * *

UNITED STATES PATENT AND TRADEMARK OFFICE
CERTIFICATE OF CORRECTION

PATENT NO. : 7,277,051 B2
APPLICATION NO. : 10/527990
DATED : October 2, 2007
INVENTOR(S) : Falk et al.

Page 1 of 1

It is certified that error appears in the above-identified patent and that said Letters Patent is hereby corrected as shown below:

In Fig. 4A, Sheet 5 of 11, for Tag "401", delete " 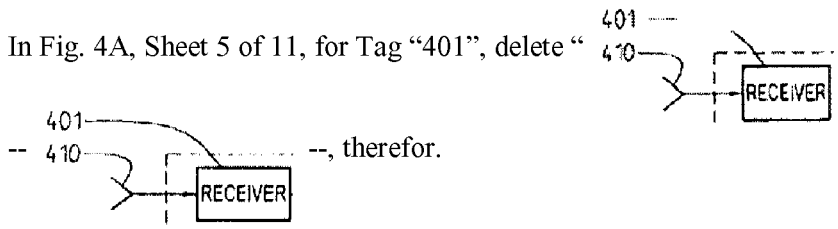 " and insert --  --, therefor.

In Column 8, Line 22, delete "AND" and insert -- A/D --, therefor.

In Column 16, Line 27, delete "513" and insert -- 613 --, therefor.

Signed and Sealed this

Twenty-second Day of July, 2008

JON W. DUDAS
*Director of the United States Patent and Trademark Office*